United States Patent
Kumar et al.

(12) United States Patent
(10) Patent No.: US 11,166,911 B2
(45) Date of Patent: Nov. 9, 2021

(54) PARENTERAL DOSAGE FORM OF AMIODARONE

(71) Applicant: SUN PHARMACEUTICAL INDUSTRIES LIMITED, Maharashtra (IN)

(72) Inventors: Samarth Kumar, Baroda (IN); Soni Maheshkumar Parasmal, Baroda (IN); Milan Mohanbhai Vasoya, Baroda (IN); Prashant Kane, Baroda (IN); Subhas Balaram Bhowmick, Baroda (IN); Rajamannar Thennati, Baroda (IN)

(73) Assignee: SUN PHARMACEUTICAL INDUSTRIES LIMITED, Maharashtra (IN)

( * ) Notice: Subject to any disclaimer, the term of this patent is extended or adjusted under 35 U.S.C. 154(b) by 0 days.

(21) Appl. No.: 16/081,896

(22) PCT Filed: Mar. 3, 2017

(86) PCT No.: PCT/IN2017/050081
§ 371 (c)(1),
(2) Date: Aug. 31, 2018

(87) PCT Pub. No.: WO2017/149552
PCT Pub. Date: Sep. 8, 2017

(65) Prior Publication Data
US 2019/0070110 A1 Mar. 7, 2019

(30) Foreign Application Priority Data
Mar. 4, 2016 (IN) .............................. 201621007739

(51) Int. Cl.
*A61K 31/343* (2006.01)
*A61K 47/40* (2006.01)
*A61K 9/08* (2006.01)
*A61K 9/00* (2006.01)

(52) U.S. Cl.
CPC ............. *A61K 9/08* (2013.01); *A61K 9/0019* (2013.01); *A61K 31/343* (2013.01); *A61K 47/40* (2013.01)

(58) Field of Classification Search
CPC .......................... A61K 31/343; A61K 9/0019
See application file for complete search history.

(56) References Cited

U.S. PATENT DOCUMENTS

| 6,869,939 B2 * | 3/2005 | Mosher | A61K 9/0019 514/469 |
| 2012/0142768 A1 * | 6/2012 | Mosher | A61K 9/0019 514/469 |

FOREIGN PATENT DOCUMENTS

| WO | WO 03/092590 A2 | 11/2003 |
| WO | WO 2011/156481 A2 | 12/2011 |

OTHER PUBLICATIONS

International Search Report and Written Opinion for PCT/IN2017/050081 dated Jun. 13, 2017.
Parmar et al., International Journal of Pharmaceutical Compounding, vol. 1, No. 5, Sep./Oct. 1997, pp. 347-348.
Helm et al., "Complexation of Dihydroergotamine Mesylate with Cyclodextrin Derivatives: Solubility and Stability in Aqueous Solution," European Journal of Pharmaceutical Sciences, 1995, pp. 195-201, Elsevier.
Holvoet et al., "Inclusion Complexation of Diazepam with Different Cyclodextrins in Formulations for Parenteral Use," 2005, pp. 598-603, Pharmazie 60.
Jacobs et al., "Ready-To-Use Parenteral Amiodarone: A Feasibility Study Towards a Long-term Stable Product Formulation," BMJ, 2017, 24, pp. 110-114, Eur J Hosp Pharm.

* cited by examiner

*Primary Examiner* — Craig D Ricci
*Assistant Examiner* — Janet L Coppins
(74) *Attorney, Agent, or Firm* — Blank Rome LLP

(57) ABSTRACT

The present invention provides a parenteral dosage form consisting essentially of a solution filled in a container, the solution comprising amiodarone or its pharmaceutically acceptable salt and a sulfo-alkyl ether beta-cyclodextrin in an aqueous vehicle, wherein the solution has a pH in the range of about 2.4 to 3.9 and further wherein the dosage form is sterilized by subjecting the filled container to autoclaving.

13 Claims, No Drawings

PARENTERAL DOSAGE FORM OF AMIODARONE

FIELD OF THE INVENTION

The present invention relates to a parenteral dosage form of amiodarone or its pharmaceutically acceptable salt. The dosage form is a solution which is sterilized by autoclaving.

BACKGROUND OF THE INVENTION

Amiodarone hydrochloride is (2-butyl-3-benzo-furanyl)[4-[2-(diethylamino)ethoxy]-3,5-diiodophenyl]methanone hydrochloride and have the following structural formula

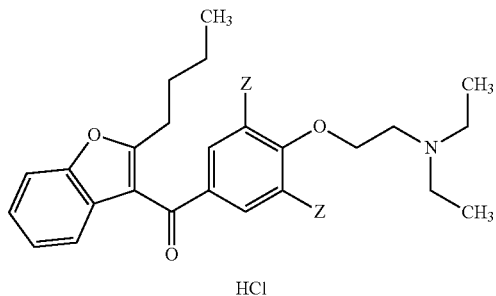

Amiodarone HCl is a white to slightly yellow crystalline powder, and is very slightly soluble in water (0.2-0.5 mg/ml). Amiodarone is a class III antiarrhythmic drug. Approved products include tablets (oral) as well as injections. Two injectable dosage forms approved in the United States include—CORDARONE® and NEXTERONE®. These are indicated for initiation of treatment and prophylaxis of frequently recurring ventricular fibrillation (VF) and hemodynamically unstable ventricular tachycardia (VT) in patients refractory to other therapy. CORDARONE® is an injection solution concentrate of Amiodarone, having 50 mg/ml Amiodarone hydrochloride. Each mL of the amiodarone I.V. formulation contains 50 mg of amiodarone hydrochloride, 20.2 mg of benzyl alcohol, 100 mg of polysorbate 80, and water for injection. NEXTERONE® Premixed Injection is available as a ready-to-use, nonpyrogenic, iso-osmotic solution for intravenous administration, each mL containing 1.5 mg of amiodarone HCl, USP; 15 mg Betadex Sulfobutyl Ether Sodium, NF; 0.362 mg citric acid anhydrous, 0.183 mg sodium citrate dihydrate and 42.1 mg dextrose anhydrous in water for injection. These commercially marketed products are prepared by sterile filtration and aseptic filling technology, which are generally not the preferred techniques of sterilization and are inferior to terminal sterilization methods such as autoclaving, that offers a higher confidence of sterility compliance.

Amidarone is very slightly soluble in water and is known to degrade significantly upon storage at higher temperatures (Chemical Stability of Amiodarone Hydrochloride in Intravenous Fluids, by Parmar et al. *International Journal of Pharmaceutical Compounding*, vol. 1, no. 5, September/October 1997, pp. 347-348). It is therefore difficult to prepare a stable, clear aqueous solution of amiodarone by autoclaving or terminally sterilizing the solution in an autoclave.

The use of a terminal sterilization method such as autoclaving is known to be advantageous over sterile filtration and aseptic filling as it offers a higher confidence of sterility compliance Thus, there lies an urgent need for a parenteral dosage form of amiodarone that can be sterilized by terminal sterilization process like autoclaving. It is also desirable that such a parenteral dosage form remains stable upon autoclaving and upon long term storage. The present invention precisely fulfills this need.

SUMMARY OF THE INVENTION

The present invention provides a parenteral dosage form consisting essentially of a solution filled in a container, the solution comprising amiodarone or its pharmaceutically acceptable salt and a sulfo-alkyl ether beta-cyclodextrin in an aqueous vehicle, wherein the solution has a pH in the range of about 2.4 to 3.9 and further wherein the dosage form is sterilized by subjecting the filled container to autoclaving. The present inventors were faced with a problem that aqueous solutions of amiodarone or its pharmaceutically acceptable salt whether with or without sulfo-alkyl ether beta-cyclodextrin turned hazy to cloudy when subjected to autoclaving. The inventors solved the problem by discovering that solution of amiodarone or its pharmaceutically acceptable salt and a sulfo-alkyl ether beta-cyclodextrin in an aqueous vehicle having a pH of 2.4 to 3.9 was found to remain clear upon autoclaving and upon long term storage. Further it was chemically stable upon storage.

DETAILED DESCRIPTION OF THE INVENTION

The parenteral dosage form of the present invention consists essentially of a solution filled in a container. The term "consisting essentially of a solution filled in a container" is intended to mean that the parenteral dosage form is directed to an aqueous solution that is filled into a suitable container, and excludes an emulsion or a suspension or any other form of a biphasic dispersion. It is understood that a solution is clear and not hazy or turbid.

Amiodarone is present in the solution in an amount ranging from about 0.01 mg/ml to about 50.0 mg/ml, preferably from about 0.1 mg/ml to about 10.0 mg/ml, more preferably about 0.5 mg/ml and about 2.0 mg/ml. In one preferred embodiment, amiodarone hydrochloride is present in the solution in an amount of 1.5 mg/ml. In another preferred embodiment, amiodarone hydrochloride is present in the solution in an amount of 1.8 mg/ml.

The solution used in the parenteral dosage form of the present invention comprises amiodarone or its pharmaceutically acceptable salt and a solubilizer. The solubilizer is any substance that either complexes with amiodarone and solubilizes it or it may be a substance that forms inclusion complex of amiodarone and upon autoclaving, it provides stability to the aqueous vehicle. Preferably the solubilizer is sulfo-alkyl ether β-cyclodextrin (or sulfo-alkyl ether beta-cyclodextrin) or salts thereof. Sulfo-alkyl ether β-cyclodextrins include but are not limited to sulfo-butyl ether β-cyclodextrin (SBE-CD) or its salt such as sulfo-butyl ether β-cyclodextrin sodium salt, sulfoalkyl-ether-alkyl-ether beta-cyclodextrin, sulfoalkyl-ether-hydroxyalkyl-ether beta-cyclodextrin or mixtures thereof. In preferred embodiments, the solubilizer is sulfobutyl ether-beta-cyclodextrin or its sodium salt. It may have varied degree of substitution, preferably varying from 4 to 7, more preferably from 6.2 to 7.0. A particularly preferred solubilizer is sulfobutyl ether-7-beta-cyclodextrin having an average of about 7 substituents per cyclodextrin molecule. Another preferred solubilizer is sulfobutyl ether-4-beta-cyclodextrin which has a degree of substitution of about 4.

In some embodiment, amiodarone and sulfoalkyl ether β-cyclodextrin (SAE-CD) may be used in the parenteral dosage form of the present invention in a weight/weight ratio ranging from about 1:0.3 to about 1:80. In one embodiment, the more preferred weight/weight ratio is about 1:10. In one embodiment, the solution according to the present invention comprises amiodarone and a sulfo-butyl ether β-cyclodextrin (SBE-CD) as a solubilizer, in which the weight ratio of amiodarone or its pharmaceutically acceptable salt and sulfo-butyl ether β-cyclodextrin ranges from about 1:0.3 to about 1:80.

The solution used in the parenteral dosage form of the present invention comprises amiodarone or its pharmaceutically acceptable salt and a sulfo-alkyl ether beta-cyclodextrin in an aqueous vehicle, wherein the solution has a pH in the range of about 2.4 to 3.9. The pH may be adjusted by using one or more buffers or pH adjusting agents. The pH of the solution is in the range of about 2.4 to 3.9, preferably in the range of about 3.2 to 3.8, for example 3.25, 3.3, 3.35, 3.4, 3.45, 3.5, 3.55, 3.6, 3.65, 3.7 and 3.75. In one embodiment, the solution of the present invention has a pH of 3.5. When buffers are used to adjust the pH, it may be selected from a group of pharmaceutically acceptable buffer systems such as citrate buffer, tartrate buffer, phosphate buffer, acetate buffer, lactate buffer, glycine buffer or mixtures thereof or and the like. These includes buffers containing any of the commonly used compounds or a mixture of compounds such as citric acid, sodium citrate, potassium citrate, tartaric acid, sodium tartrate, phosphoric acid, sodium phosphate, disodium hydrogen phosphate, sodium dihydrogen phosphate, potassium phosphate, potassium hydrogen phosphate, potassium dihydrogen phosphate, acetic acid, sodium acetate, lactic acid, sodium lactate, glycine, sodium hydroxide, potassium hydroxide, hydrochloric acid etc. The pH of the solution is critical for physical stability. The solution after autoclaving remains clear when the pH is in the range of about 2.4 to 3.9. Outside this pH range, the solution shows haziness or turbidity upon autoclaving.

In one embodiment the solution used in the parenteral dosage form may comprise a tonicity adjusting agent or osmogent. The osmogent may be used in suitable amounts such that the solution has an osmolality in the range of about 250-500 mOsm/kg, preferably 270-330 mOsm/kg. The osmogent that may be used in the solution of the present invention may be selected from, but not limited to, dextrose, sodium chloride, potassium chloride, calcium chloride, mannitol, sorbitol, sucrose and the like and mixtures thereof. Alternatively in one embodiment, the parenteral dosage form may comprise isotonic diluent selected from a group of pharmaceutically acceptable diluents such as dextrose solution and sodium chloride solution.

The solution of the parenteral dosage form of the present invention may further comprise other parenterally acceptable additives. The additives which may be used in the aqueous solution of this invention include co-solvents, chelating agents, antioxidants, buffers and isotonic diluents, which in the usual quantities added do not affect to the clarity and stability of the solution.

In one preferred embodiment, the solution present in the parenteral dosage form of the present invention is free of added co-solvents. Alternatively, co-solvents may be used and may be selected from a group of pharmaceutically acceptable compounds such as glycerin, propylene glycol, polyethylene glycol of low molecular weight series. In particularly preferred embodiments, the solution is free of preservatives. In one preferred embodiment the solution is free of anti-oxidants. In another embodiment, antioxidants may be used and are selected from a group of pharmaceutically acceptable compounds such as sodium metabisulphite, acetylcysteine, cysteine, ascorbic acid, alpha-tocopherol and the like. In one embodiment, the solution may contain a chelating agent such as edetic acid, disodium edetate, ethylene diamine tetraacetic acid and salts thereof. Preferably, the solution in the parenteral dosage form of the present invention is free of preservatives and antioxidants.

In one embodiment, the solution in the parenteral dosage form according to the present invention may be purged with an inert gas such as nitrogen or argon to substantially remove the dissolved oxygen. In another embodiment, the headspace of the container may be replaced by an inert gas.

The parenteral dosage form consists essentially of a solution of amiodarone or its pharmaceutically acceptable salt filled in a container. The volume capacity of each unit of the container may range from about 50 ml to about 500 ml. The aqueous solution may present in the infusion containers in volumes ranging from about 50 ml to 500 ml per infusion container, such as for example 50 ml, 75 ml, 100 ml, 120 ml, 125 ml, 140 ml, 150 ml, 160 ml, 175 ml, 180 ml, 190 ml, 200 ml, 220 ml, 225 ml, 240 ml, 250 ml, 260 ml, 275 ml, 280 ml, 290 ml, 300 ml, 320 ml, 325 ml, 340 ml, 350 ml, 360 ml, 375 ml, 380 ml, 390 ml, 400 ml, 420 ml, 425 ml, 430 ml, 440 ml, 450 ml, 460 ml, 470 ml, 475 ml, 480 ml, 490 ml or 500 ml. According to one preferred embodiment the volume of solution filled in the container is 100 ml. According to another preferred embodiment the volume of solution filled in the container is 200 ml. According to another preferred embodiment the volume of solution filled in the container is 300 ml.

The containers of the parenteral dosage form may be rigid or flexible. The container is preferably a single compartment container, suitable for parenteral infusion. The container may be single layered or multi layered. In one embodiment, the containers have a single outlet meant for withdrawal of the aqueous solution from the container while being administered. In one embodiment, the parenteral dosage form of the present invention comprises a flexible container which is made up of a plastic material or other polymeric material. Non limiting examples of the flexible container include an infusion bag, a flexible infusion pouch, a soft bag, an infusion bottle, a film, or a plastic pre-filled syringe. The plastic or any other polymeric material of which the flexible container is made, may be selected from, but not limited to, cyclo olefin polymers, cyclo olefin copolymers, polyolefin based polymers such as polyethylene polymers; polyamides, polyesters, ethylene vinyl acetate, modified polyolefin-polyethylene polymers or styrene-polyolefin based polymers and block co-polymers thereof. These flexible containers may have one or more layers of plastic/polymeric materials. Preferably, the flexible container is made up of a material comprising cyclo olefin polymers or cyclo olefin copolymers as the product contact layer. In preferred embodiments, the plastic or polymeric material which constitute the flexible container have an oxygen transmission rate ranging from about 100 to 1400 (ml or $cm^3$)/($m^2$.24 hour.atm), a water vapour transmission rate of about 0.2 to 6.0 g/($m^2$.day) and a carbon dioxide transmission rate of about 3000 to 6500 (ml or $cm^3$)/($m^2$.24 hour.atm). In preferred embodiment, the flexible container is made up of a material comprising a polymer of cyclic olefin such as cyclooolefin homopolymer or cycloolefin copolymer or mixture thereof. Specifically, in a particularly preferred embodiment, the parenteral dosage form comprises a flexible infusion bag container having an inner layer made up of a cycloolefin polymer, a middle layer made up of linear low density polyethylene polymer and an outer layer made up of low density polyethylene polymer. The inner layer remains in contact with the aqueous solution. Such containers are available commercially and are manufactured by Hosokawa as Polyelite EHC® film bag. These containers have a water vapour transmission rate of 2 g ($m^2$.day) when measured at (40° C./90% relative humidity); oxygen transmission rate of 570 ml/($m^2$.24 hour.atm) when measured at (23° C./0% relative humidity) and carbon dioxide transmission rate of 3400 ml/($m^2$.24 hour.atm) when measured at 23° C./0% relative humidity.

In alternate embodiment, the flexible container is made up of an outer layer of polyamide 11, a middle tie of modified polyolefin and an inner layer of linear low density polyethylene. These containers have a water vapour transmission rate of 2 g ($m^2$.day) when measured at (40° C./90% relative humidity); oxygen transmission rate of 900 ml/($m^2$.24 hour.atm) when measured at (23° C./0% relative humidity) and carbon dioxide transmission rate of 600 ml/($m^2$.24 hour.atm) when measured at 23° C./0% relative humidity. Such containers are available commercially and are manufactured by Hosokawa as Polyelite AE-1®. In another embodiment, the flexible container is made up of an outer layer of polypropylene polymer with styrene-ethylene-butylene (SEB) block copolymer and a middle and inner layer made up of polypropylene based polyolefin polymer with styrene-ethylene butylene block copolymer. Such containers are available commercially under the brand name Inerta 103® and are manufactured by Technoflex. These containers have a water vapour transmission rate of 0.62 g ($m^2$.day) when measured at 23° C./60% relative humidity; oxygen permeability of 1110 ml/($m^2$.24 hour.atm) when measured at 23° C./40% relative humidity and carbon dioxide transmission rate of 5149 ml/($m^2$.24 hour.atm). In another embodiment, the flexible container is made up of multilayer polyolefin film having layers from outside to inside made up of CPET-Tie-PE-Tie-EPC. Such containers are available as M312 and M312A® films by Sealer Air Corporation. These containers have a water vapour transmission rate of 5.0 g ($m^2$.day) when measured at 38° C./100% relative humidity; oxygen transmission rate of 1315 $cm^3$/($m^2$.24 hour.atm) when measured at 73° F./0% relative humidity and carbon dioxide transmission rate of 3945 $cm^3$/($m^2$.24 hour.atm). In one specific embodiment, the flexible containers, particularly an infusion bag, may include a Minitulipe® infusion port which is an infusion connector having three assembled parts including a central stopper made up of chlorobutyl rubber (latex free); an upper breakable part and a bottom part, both made up of polycarbonate. In one embodiment, the flexible container contains a delivery port end for insertion of an infusion set cannula/needle. In one embodiment, the flexible container/bag and the delivery port connecting to the infusion needle form a system whereby during administration of the solution to the patient the vacuum created by outgress of solution is accommodated by the elasticity or flexibility of the infusion bag instead of ingress of external non-sterile air. The dosage form can advantageously maintain the sterility of the solution until it reaches the patient. Further in one embodiment, the container may be a rigid container such as those made up of type I borosilicate glass, rigid cycloolefin polymers or cycloolefin copolymers and the like. The rigid container may be a vial or a bottle or a prefilled syringe (PFS). In one embodiment, the container may be optionally further packaged in a secondary packaging. The secondary packaging may comprise a second container such as a pouch or overwrap or carton. In one preferred embodiment, the secondary packaging pouch or overwrap or carton is made up of a suitable light protective material such as aluminum. The secondary packaging may further comprise an oxygen scavenger or alternatively an oxygen scavenging layer may be present in the primary or secondary container.

The present invention further relates to a process for preparing the parenteral dosage form consisting essentially of a solution filled in a container, the solution comprising amiodarone or its pharmaceutically acceptable salt and a sulfo-alkyl ether beta-cyclodextrin in an aqueous vehicle, wherein the solution has a pH in the range of about 2.4 to 3.9 and further wherein the dosage form is sterilized by subjecting the filled container to autoclaving.

Particularly, the method of preparing the parenteral dosage form of the present invention involves the steps of:
1) preparing an acidic buffer or a solution of pH adjusting agent, the solution having a pH in the range of 2.4 to 3.9,
2) adding a solubilizer like sulfobutylether beta-cyclodextrin to the acidic buffer solution of step 1,
3) optionally, warming the solution of step 2,
4) adding amiodarone or its pharmaceutically acceptable salt to the solution of step 3 and dissolving it under continuous stirring,
5) optionally, warming the solution of step 4 to 55-60'C until the solution is a clear solution,
6) adding specified quantity of an osmogent to the above solution,
7) adjusting the pH of the solution in the range of 2.4 to 3.9,
8) filtering the solution of step 7 through a 0.2μ filter,
9) filling the filtered solution into a container and sealing it with the suitable stopper.
10) subjecting the filled and sealed container to autoclaving, i.e. steam sterilization in an autoclave,
11) optionally, covering the sterilized filled and sealed containers with a secondary packaging.

The parenteral dosage form of the present invention is 'stable'. As used herein, the term 'stable' means that the dosage form of the present invention is physically as well as chemically stable upon autoclaving and also stable for prolonged period of time such as for at least 6 months, preferably 12 months, more preferably for 24 months when stored at room temperature (25° C./40% relative humidity). The physically stability implies that the solution of amiodarone or its pharmaceutically acceptable salt in the parenteral dosage form of the present invention remains clear and colourless with no signs or haziness or turbidity upon autoclaving and upon storage. The chemical stability implies that the assay of amiodarone or its pharmaceutically acceptable salt remains within 90-110% by weight of the label claim, the content of total impurities remain within 0-2.0% by weight and the content of known impurities or single maximum unknown impurity remains within 0-0.2% by weight of amiodarone or its pharmaceutically acceptable salt. The impurities are expressed as % by weight of amiodarone or its pharmaceutically acceptable salt.

In the context of this specification "comprising" is to be interpreted as "including". Aspects of the invention comprising certain elements are also intended to extend to alternative embodiments "consisting" or "consisting essentially" of the relevant elements.

Where technically appropriate, embodiments of the invention may be combined.

Embodiments are described herein as comprising certain features/elements. The disclosure also extends to separate embodiments consisting or consisting essentially of said features/elements.

Any embodiments specifically and explicitly recited herein may form the basis of a disclaimer either alone or in combination with one or more further embodiments.

Hereinafter, the invention will be more specifically described by way of Examples. The examples are not intended to limit the scope of the invention and are merely used as illustrations.

Examples 1-5

The Example 1-8 describes the parenteral dosage form of amiodarone according to preferred embodiments of the present invention. The details of aqueous solution of amiodarone are given below in Table 1 and 2:

TABLE 1 aqueous solution of amiodarone according to Example 1

| Ingredients | Amount in mg/ml |
| --- | --- |
| Amiodarone hydrochloride | 1.5-1.8 |
| Sulfo-butyl ether beta-cyclodextrin | 15-18 |
| Citric acid anhydrous | 0.362 |
| Sodium citrate anhydrous | 0.183 |
| Dextrose | 41.4-42.1 |
| Adjust pH to | 2.4 to 3.9 |
| Water for injection | q.s. |

TABLE 2 aqueous solution of amiodarone using sulfo-butyl ether beta-cyclodextrin and having pH in the range of 2.4 to 3.9

| Ingredients | Example 2 | Example 3 | Example 4 | Example 5 | Example 6 | Example 7 | Example 8 |
| --- | --- | --- | --- | --- | --- | --- | --- |
| | Amount in mg/ml | | | | | | |
| Amiodarone hydrochloride | 1.5 | 1.8 | 1.5 | 1.5 | 1.5 | 1.5 | 1.5 |
| Sulfo-butyl ether beta-cyclodextrin | 15 | 18 | 15 | 15 | 15 | 15 | 15 |
| Citrate buffer (citric acid anhydrous + Sodium citrate anhydrous | 0.362 0.183 | 0.362 0.183 | — — | — — | — — | — — | — — |
| Acetic/phosphoric/ lactic/tartaric acid/ hydrochloric acid/citric acid Sodium hydroxide | — | — | q.s. to pH 3.25 | q.s. to pH 3.75 | q.s. to pH 3.9 | q.s. to pH 2.4 | q.s. to pH 2.6 |
| Dextrose | 42.1 | 41.4 | 42.1 | 42.1 | 42.1 | 42.1 | 42.1 |
| pH adjusted to | 3.6 | 3.5 | 3.25 | 3.75 | 3.9 | 2.4 | 2.6 |
| Water for injection | q.s. | q.s. | q.s. | q.s. | q.s. | q.s. | q.s. |

Procedure:
1) A portion of the total water for injection was collected in a stainless steel container.
2) Accurately weighed quantity of citric acid anhydrous was added to step 1 with stirring.
3) Accurately weighed quantity of sodium citrate dihydrate was added to step 2 with stirring.
4) Accurately weighed quantity of Sulfobutylether beta-cyclodextrin sodium was added to step 3 with stirring.
5) The solution of step 4 was heated in water-bath till the 55-65° C. temperature is achieved.
6) Amiodarone HCl was added to the above bulk solution of step 5 and dissolved under continuous stirring. Temperature of the solution was maintained to 55-60'C until the solution was visibly clear.
7) The clear solution was allowed to cool at room temperature.
8) Dextrose was added to the above solution under stirring.
9) The pH of the solution was adjusted to 3.6 (Example 2), 3.5 (Example 3), 3.25 (Example 4), 3.75 (Example 5), 3.9 (Example 6), 2.4 (Example 7) and 2.6 (Example 8).
10) Volume was made-up with water for injection and stirred to mix the solution.
11) Solution was filtered through 0.2μ filter and collected in stainless steel container.
12) Filtered solution was filled in the Infusion bag and sealed with the suitable stopper.
13) Filled and sealed bags were subjected to the terminal sterilization by autoclaving at 121° C. for 15 minutes in an autoclave.
14) The sterilized filled bags were overwrapped with secondary packaging material.

The parenteral dosage form having the aqueous solution of amiodarone prepared according to example 1 to 8 and filled in the containers, when subjected to terminal sterilization by autoclaving, were found to be clear and colourless without any signs of haziness immediately after autoclaving. So also, when such parenteral dosage forms were stored over a prolonged period of time (for at least 6 months) at room temperature (25° C./40% relative humidity) as well as at accelerated storage stability conditions such as at 40° C./25% relative humidity, showed no signs of haziness i.e. the parenteral dosage form was physically stable.

Example 9

The parenteral dosage forms of Example 2 and 3 were checked for chemical stability upon storage at room temperature (25° C./40% relative humidity) and at 40° C./25% relative humidity (accelerated storage stability condition). The assay of amiodarone (% of label claim), highest unknown impurity and total impurities upon storage were determined at different time points and are tabulated below in Table 3 and 4:

These solutions so prepared were filled into infusion bags and the filled and sealed infusion bags were subjected to the terminal sterilization by autoclaving at 121° C. for 15

TABLE 3

Stability study results for dosage form of example 2:

| Tests | Stability data at different time points | | | | | | | | |
|---|---|---|---|---|---|---|---|---|---|
| | | 25° C./40% RH | | | | 40° C./25% RH | | | |
| Parameters | Initial | 1 M* | 2 M | 3 M | 6 M | 1 M | 2 M | 3 M | 6 M |
| Assay (%) | 99.63 | 96.99 | 96.9 | 98.78 | 98.07 | 96.41 | 96.55 | 98.35 | 98.54 |
| Single maximum unknown impurity (RRT) | 0.03 (1.08) | 0.045 (1.06) | 0.026 (0.92) | 0.026 (0.9) | 0.033 (0.91) | 0.048 (0.92) | 0.025 (0.92) | 0.035 (1.07) | 0.041 (0.08) |
| Total impurities % | 0.161 | 0.27 | 0.168 | 0.234 | 0.241 | 0.276 | 0.19 | 0.284 | 0.25 |
| pH | 3.55 | 3.51 | 3.55 | 3.51 | 3.41 | 3.5 | 3.55 | 3.51 | 3.34 |

M*—Month;
RH—Relative Humidity

TABLE 4

Stability study results for dosage form of example 3:

| Test Parameters | Stability data at different time points | | | | | | | |
|---|---|---|---|---|---|---|---|---|
| | | 25° C./40% RH | | | | 40° C./25% RH | | |
| | Initial | 1 M* | 2 M | 3 M | 6 M | 1 M | 2 M | 6 M |
| Assay (%) | 99.94 | 98.81 | 96.76 | 99.32 | 99.68 | 96.91 | 96.91 | 99.04 |
| Single maximum unknown Impurity (RRT) | 0.026 (1.08) | 0.045 (1.06) | 0.026 (0.92) | 0.034 (1.08) | 0.031 (0.91) | 0.049 (1.06) | 0.029 (0.92) | 0.044 (0.08) |
| Total impurities % | 0.171 | 0.327 | 0.19 | 0.251 | 0.246 | 0.268 | 0.206 | 0.27 |
| pH | 3.49 | 3.51 | 3.57 | 3.53 | 3.35 | 3.52 | 3.58 | 3.39 |

M* Month;
RH—Relative Humidity

The above data shows that the assay of amiodarone was within 95%-105% upon storage. The content of individual known impurities remained below 0.2% by weight, the content of single maximum unknown impurity remained below 0.2% by weight and the content of total impurities remained below 0.5% by weight of amiodarone. Thus, it can be concluded that the parenteral dosage forms of Example 2 and Example 3, were found to be chemically stable when stored at room temperature (25° C./40% relative humidity) and at 40° C./25% relative humidity (accelerated storage stability condition) for a prolonged period of at least 6 months.

Comparative Example 1

The solution of amiodarone using sulfo-butyl ether beta-cyclodextrin was prepared similar to example 1. However, the pH adjustment was done at pH values of 2.0, 2.2, 2.3, 4.0, 4.25, 4.5 and 5.5. The pH was adjusted using an inorganic acid (acetic acid/phosphoric acid/lactic acid/tartaric acid/citric acid/hydrochloric acid) along with addition of sodium hydroxide in amounts sufficient to achieve the specified pH values.

minutes in an autoclave. Upon autoclaving, the solutions showed haziness or turbidity and were therefore unstable.

The pH of the solution is thus critical and the solution after autoclaving remains clear only when the pH is in the range of about 2.4 to 3.9. Outside this pH range, the solution upon autoclaving shows haziness or turbidity.

Comparative Examples 2-3

TABLE 5

Composition of comparative examples 2 and 3 using cyclodextrins other than sulfo-alkyl ether beta-cyclodextrin

| Ingredients | Comparative example 2 | Comparative example 3 |
|---|---|---|
| | Mg per ml | |
| Amiodarone hydrochloride | 1.5 | 1.8 |
| Hydroxy propyl-beta-cyclodextrin (HP) molecular weight-1493 | 10.3 | — |
| Hydroxy propyl-beta-cyclodextrin (HPB) molecular weight-1395 | — | 59 |

TABLE 5-continued

Composition of comparative examples 2 and 3 using cyclodextrins other than sulfo-alkyl ether beta-cyclodextrin

| Ingredients | Comparative example 2 | Comparative example 3 |
|---|---|---|
| | Mg per ml | |
| Citric acid anhydrous | 0.362 | 0.362 |
| Sodium citrate anhydrous | 0.183 | 0.183 |
| Dextrose | 42.1 | — |
| Water for injection | q.s. | q.s. |
| pH | 3.52 | 3.51 |

The parenteral dosage form of amiodarone was attempted using different grades of cyclodextrins, namely, hydroxypropyl-beta-cyclodextrin (HP) of molecular weight 1493 and hydroxypropyl-beta-cyclodextrin (HPB) of molecular weight 1395. The dosage form was prepared as per the procedure of Example 2.

It was found that the aqueous solution of comparative example 2 and comparative example 3 when filled into either glass vial or plastic containers and subjected to autoclaving at 121° C. for 15 minutes, yielded unstable solution, in that the solutions turned hazy.

Surprisingly, the aqueous solutions of Example 1 to 8, which used sulfo-alkyl ether beta-cyclodextrin and had a pH in the range of 2.4 to 3.9, when filled into either glass vial or plastic containers and subjected to autoclaving at 121° C. for 15 minutes, yielded stable solutions, which were clear and colourless without any sign of haziness, immediately after autoclaving as well as upon storage for prolonged period of time. Further their chemical analysis revealed the solutions were chemically stable when stored over a prolonged period of time.

Comparative Example 4

TABLE 6

Aqueous solution of amiodarone hydrochloride without cyclodextrin and having pH of about 2.8

| Ingredients | Amount in mg/ml |
|---|---|
| Amiodarone hydrochloride | 1.5 |
| Acetic acid | 9.0 |
| Glycerine | 13.8 |
| pH adjusting agent q.s to pH | 2.81 |
| Water for Injection | q.s. |

Preparation: Nitrogen purged water for injection at temperature between 55-70° C. was taken and acetic acid was gradually added and dissolved under stirring in water for injection. The temperature of the solution was maintained at 55-70° C. during stirring. To this solution, glycerine was gradually added and dissolved by stirring. The temperature of the solution was maintained at 55-70° C. To this bulk solution, the active agent amiodarone hydrochloride was added gradually and dissolved under stirring. The temperature of the solution was maintained at 55-70° C. during stirring. The solution was allowed to stabilize and clarity of the solution was ensured visually. The solution was then cooled to 20-25° C. and the pH was checked which was about 2.8. The solution was then filled in an infusion bag (plastic container) and subjected to autoclaving at 121° C. for 15 minutes. It was found that the the solution turned hazy and was therefore unstable.

The invention claimed is:

1. An autoclaved parenteral dosage form consisting essentially of a solution filled in a container, the solution comprising about 0.1 mg/ml to about 10.0 mg/ml of amiodarone or a pharmaceutically acceptable salt thereof and a sulfoalkyl ether beta-cyclodextrin in an aqueous vehicle, wherein the solution has a pH in the range of about 2.4 to about 3.9, and further wherein the dosage form is sterilized by subjecting the filled container to autoclaving, and wherein said solution remains clear and the dosage form remains stable during storage in the container at room temperature for at least 6 months after sterilization by autoclaving.

2. The autoclaved parenteral dosage form according to claim 1, wherein the sulfo-alkyl ether beta-cyclodextrin is sulfobutyl-ether beta-cyclodextrin.

3. The autoclaved parenteral dosage form according to claim 1, wherein the solution is free of preservatives and antioxidants.

4. The autoclaved parenteral dosage form according to claim 1, wherein the amiodarone or the pharmaceutically acceptable salt thereof is present in the solution at about 0.5 mg/ml to about 2.0 mg/ml.

5. The autoclaved parenteral dosage form according to claim 4, wherein the amiodarone or the pharmaceutically acceptable salt thereof is present in the solution at about 1.5 mg/ml.

6. The autoclaved parenteral dosage form according to claim 4, wherein the amiodarone or the pharmaceutically acceptable salt thereof is present in the solution at about 1.8 mg/ml.

7. The autoclaved parenteral dosage form according to claim 1, wherein the container is made of a material comprising a cyclo olefin polymer.

8. The autoclaved parenteral dosage form according to claim 1, wherein the solution comprises about 1.5 mg/m of amiodarone hydrochloride.

9. The autoclaved parenteral dosage form according to claim 1, wherein the solution comprises 1.5 mg/ml of amiodarone hydrochloride, 15 mg/ml of sulfo-butyl ether beta-cyclodextrin, 0.362 mg citric acid anhydrous, 0.183 mg/ml sodium citrate dihydrate, and 42.1 mg/ml dextrose.

10. The autoclaved parenteral dosage form according to claim 1, wherein the solution comprises about 1.8 mg/ml of amiodarone hydrochloride.

11. The autoclaved parenteral dosage form according to claim 1, wherein the solution comprises 1.8 mg/ml of amiodarone hydrochloride, 18 mg/ml of sulfo-butyl ether beta-cyclodextrin, 0.362 mg citric acid anhydrous, 0.183 mg/ml sodium citrate dihydrate, and 4,4 mg/ml dextrose.

12. The autoclaved parenteral dosage form according to claim 7, wherein the solution comprises about 1.5 mg/ml of amiodarone hydrochloride.

13. The autoclaved parenteral dosage form according to claim 7, wherein the solution comprises about 1.8 mg/ml of amiodarone hydrochloride.

* * * * *